(12) United States Patent
Sprague

(10) Patent No.: US 8,847,778 B2
(45) Date of Patent: *Sep. 30, 2014

(54) PSYCHOPHYSIOLOGICAL TOUCH SCREEN STRESS ANALYZER

(71) Applicant: Phillip R. Sprague, San Diego, CA (US)

(72) Inventor: Phillip R. Sprague, San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/960,690

(22) Filed: Aug. 6, 2013

(65) Prior Publication Data

US 2013/0324805 A1 Dec. 5, 2013

Related U.S. Application Data

(63) Continuation of application No. 13/610,007, filed on Sep. 11, 2012, now Pat. No. 8,502,691, which is a continuation of application No. 12/206,703, filed on Sep. 8, 2008, now Pat. No. 8,264,364.

(51) Int. Cl.
G08B 21/00 (2006.01)
A61B 5/00 (2006.01)
A61B 5/16 (2006.01)

(52) U.S. Cl.
CPC ............... *A61B 5/4884* (2013.01); *A61B 5/164* (2013.01); *A61B 5/16* (2013.01)
USPC .......................................... 340/665; 600/301

(58) Field of Classification Search
CPC ........ A61B 5/16; A61B 5/164; A61B 5/4884; G02B 6/32; G02B 6/4204
USPC .................. 340/665, 10.5; 600/301; 715/864; 601/49, 148, 154
See application file for complete search history.

(56) References Cited

U.S. PATENT DOCUMENTS

| | | | | |
|---|---|---|---|---|
| 5,455,566 A | * | 10/1995 | Conway | 340/573.1 |
| 6,007,340 A | * | 12/1999 | Morrel-Samuels | 434/236 |
| 7,192,387 B2 | * | 3/2007 | Mendel | 482/8 |
| 7,278,975 B2 | * | 10/2007 | McCamish et al. | 600/587 |
| 8,033,996 B2 | * | 10/2011 | Behar | 600/300 |
| 2006/0244732 A1 | * | 11/2006 | Geaghan | 345/173 |
| 2008/0009393 A1 | * | 1/2008 | Glusco | 482/8 |
| 2008/0195980 A1 | * | 8/2008 | Morris | 715/864 |
| 2008/0224101 A1 | * | 9/2008 | Niu et al. | 252/511 |
| 2009/0281450 A1 | * | 11/2009 | Reichow et al. | 600/558 |
| 2010/0060461 A1 | * | 3/2010 | Sprague | 340/573.1 |
| 2011/0025311 A1 | * | 2/2011 | Chauvin et al. | 324/207.25 |

* cited by examiner

Primary Examiner — Benjamin C Lee
Assistant Examiner — Sigmund Tang
(74) Attorney, Agent, or Firm — Pattric J. Rawlins; Procopio, Cory, Hargreaves & Savitch LLP

(57) ABSTRACT

The Psychophysiological Touch Screen Stress Analyzer is capable of capturing information on how a person emotionally reacts to a series of verbal, visual, or written stimulus when the person touches the touch screen computer monitor in response to the stimulus.

11 Claims, 2 Drawing Sheets

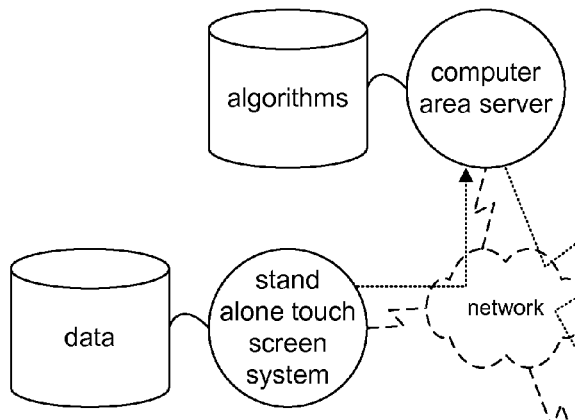
FIG. 9
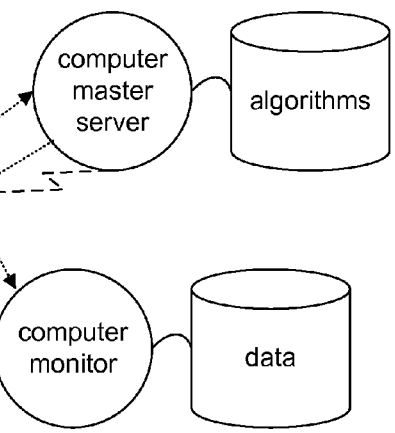
FIG. 10
FIG. 8
FIG. 11
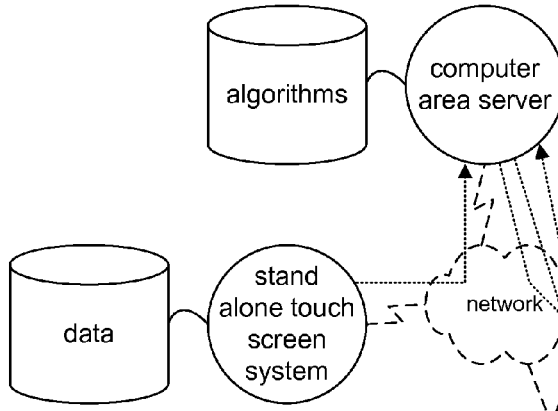
FIG. 13
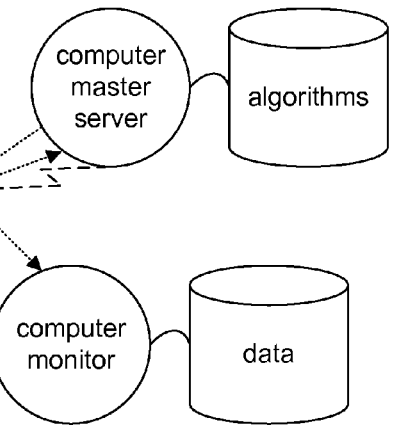
FIG. 14
FIG. 12
FIG. 15

PSYCHOPHYSIOLOGICAL TOUCH SCREEN STRESS ANALYZER

RELATED APPLICATION

The present application is a continuation of U.S. patent application Ser. No. 13/610,007 filed 11 Sep. 2012 and issued as U.S. Pat. No. 8,502,691 on 6 Aug. 2013; which is a continuation of U.S. patent application Ser. No. 12/206,703 filed 8 Sep. 2008, issued as U.S. Pat. No. 8,264,364 issued on 11 Sep. 2012, each of which is incorporated herein by reference in its entirety.

BACKGROUND

1. Field of the Invention

This invention generally relates to computerized verification of information provided by a person and more particularly relates the measurement of a person's touch response for the purpose of verification of information provided by the person.

2. Related Art

Current truth verification methods, based on the voice stress analysis which measures emotional stress in speech by detecting the presence of vibratto or rapid modulation of the phonation constituent within the speech signal envelope. Polygraph techniques rely upon the measurement of several physiological characteristics to discriminate whether a truth or a lie is expressed. These measurements include skin resistivity, blood pressure, heart rate and respiration rate. The voice stress analyzer and polygraph measure the emotional reaction of a person to a stimulus.

The Neural Basis of an Emotional Reaction

Theoretical Traditions in Emotion Research:

Theories about emotions stretch back at least as far as the Ancient Greek Stoics, as well as Plato and Aristotle. We also see sophisticated theories in the works of philosophers such as René Descartes, Baruch Spinoza and David Hume. More recent theories of emotions tend to be informed by advances in empirical research. Often theories are not mutually exclusive and many researchers incorporate multiple perspectives in their work.

Somatic Theories of Emotion:

Somatic theories of emotion claim that bodily responses rather than judgments are essential to emotions. The first modern version of such theories comes from William James in the 1880s. The theory lost favor in the 20th Century, but has regained popularity more recently thanks largely to theorists such as Antonio Damasio, Joseph LeDoux and Robert Zajonc who are able to appeal to neurological evidence.

The James-Lange Theory:

William James in the article 'What is an Emotion?' (Mind, 9, 1884: 188-205) argued that emotional experience is largely due to the experience of bodily changes. These changes might be visceral, postural, or facially expressive. Danish psychologist Carl Lange also proposed a similar theory at around the same time and thus the resulting position is known as the James-Lange theory. This theory and its derivates state that a changed situation leads to a changed bodily state. As James says 'the perception of bodily changes as they occur IS the emotion.' James further claims that 'we feel sorry because we cry, angry because we strike, afraid because we tremble, and not that we cry, strike, or tremble, because we are sorry, angry, or fearful, as the case may be.'

This theory is supported by experiments in which by manipulating the bodily state, a desired emotion is induced. Such experiments also have therapeutic implications (e.g. in laughter therapy, dance therapy).

The James-Lange theory is often misunderstood because it seems counter-intuitive. Most people believe that emotions give rise to emotion-specific actions: i.e. "I'm crying because I'm sad," or "I ran away because I was scared." The James-Lange theory, conversely, asserts that first we react to a situation (running away and crying happen before the emotion), and then we interpret our actions into an emotional response. In this way, emotions serve to explain and organize our own actions to us.

Cognitive Theories of Emotion:

There are a number of theories of emotions that argue that cognitive activity in the form of judgments, evaluations, or thoughts are necessary in order for an emotion to occur. This, it is argued[who?], is necessary to capture the fact that emotions are about something or have intentionality. Such cognitive activity may be conscious or unconscious and may or may not take the form of conceptual processing. An influential theory here is that of Richard Lazarus (1991). A prominent philosophical exponent is Robert Solomon (e.g. The Passions, Emotions and the Meaning of Life, 1993). The theory proposed by Nico Frijda where appraisal leads to action tendencies is another example.

The Perceptual Theory:

A recent hybrid of the somatic and cognitive theories of emotion is the perceptual theory. This theory is neo-Jamesian in arguing that bodily responses are central to emotions, yet it emphasizes the meaningfulness of emotions or the idea that emotions are about something, as is recognized by cognitive theories. The novel claim of this theory is that conceptually based cognition is unnecessary for such meaning. Rather the bodily changes themselves perceive the meaningful content of the emotion as a result of being causally triggered by certain situations. In this respect emotions are held to be analogous to faculties such as vision or touch, which provide information about the relation between the subject and the world in various ways. A sophisticated defense of this view is found in philosopher Jesse Prinz's book Gut Reactions (2004) and psychologist James Laird's book Feelings: The Perception of Self (2007). Related views are also found in the work of Peter Goldie and Ronald de Sousa.

The Cannon-Bard Theory:

Main Article: Cannon-Bard Theory

Walter Cannon argued against the dominance of the James-Lange theory regarding the physiological aspects of emotions in the second edition of Bodily Changes in Pain, Hunger, Fear and Rage. Where James argued that emotional behavior often precedes or defines the emotion, Cannon and Bard argued that the emotion arises first and then stimulates typical behavior.

The Two Factor Theory:

Another cognitive theory is the Singer-Schachter theory. This is based on experiments purportedly showing that subjects can have different emotional reactions despite being placed into the same physiological state with an injection of adrenaline. Subjects were observed to express either anger or amusement depending on whether another person in the situation displayed that emotion. Hence the combination of the appraisal of the situation (cognitive) and whether participants received adrenaline or a placebo together determined the response. This experiment has been criticized in Jesse Prinz (2004) Gut Reactions.

The Component Process Model:

A recent version of the cognitive theory comes from Klaus Scherer which regards emotions more broadly as the synchronization of many different bodily and cognitive components. Emotions are identified with the overall process whereby low level cognitive appraisals, in particular the processing of relevance, trigger bodily reactions, behaviors, feelings, and actions.

SUMMARY

This device is comprised of the following components: The touch screen computer monitor that displays the stimulus and senses when the person touch the computer screen in response to the stimulus.

The touch screen computer monitor displays the stimulus in the form of statement, question, picture or video.

When the person touches the touch screen in response to the stimulus, the touch screen captures data created by the person's touch and sends that data to a computer server where the data is analyzed.

The final analysis of that data is then sent to a computer monitor that will display the intensity of the person's emotional reaction patterns to a series of stimulus. The system configuration can be setup as stand alone system computer or as a client server configuration.

This invention uses the muscle tremor reaction of a person's touch when responding to written, verbal or visual stimulus. The invention captures the time and pressure of a person's touch on a touch screen computer when responding to the stimulus. The invention converts the person's touch on the touch screen to a digital signal. The use of irrelevant questions (i.e. Is today Sunday? Do you live in the United States? Were you born in the United States? Are you a citizen of the United States?) are asked to establish a baseline response pattern. The baseline bandwidth is created from the baseline response pattern. The person is then asked relevant questions (i.e. in regards to weapons, smuggling, and terrorism). If the person reaction patterns to the relevant questions are within the baseline bandwidth then it can be assumed that the person made full disclosure concerning the relevant issue(s). However, if the person reaction patterns to the relevant questions are outside the baseline bandwidth then it can be assumed that the person did not made full disclosure concerning the relevant issues(s).

This invention is to measure a emotional reaction baseline to stimuli. This baseline is used to interpret additional results between control and relevant stimuli.

The object of this invention is to detect emotional reactions to the control and relevant stimuli.

In addition to the detecting emotional reactions to the initial stimuli, a second set of more through stimuli can be presented to the person. This second set of stimuli is more focused than first set of stimuli and targets specific control and relevant issues.

The object of this invention is to supply concerned individuals reliable information as to whether or not a person represents a potential threat to welfare of others.

BRIEF DESCRIPTION OF THE DRAWINGS

FIG. 8 is an example system where the stimuli (questions, statements, pictures) are displayed on a touch screen computer through a series of computer generated screens.

FIG. 9 is an example computer area server that is connected to the touch screen through a private network.

FIG. 10 is an example computer master server connected to a computer area server through a secure network and containing additional algorithms that will perform an analysis on the touch screen data.

FIG. 11 is an example computer monitor to display the person's emotional reaction patterns on the computer screen ranging from a low to severe reactions.

FIG. 12 is an example system where the stimuli (questions, statements, pictures) are displayed on a touch screen computer through a series of computer generated screens.

FIG. 13 is an example computer area server that is connected to the touch screen through a private network.

FIG. 14 is an example computer master server connected to a computer area server through a secure network and containing additional algorithms that will perform an analysis on the touch screen data.

FIG. 15 is an example computer monitor to display the person's emotional reaction patterns on the computer screen ranging from a low to severe reactions.

DETAILED DESCRIPTION

There are five configurations for the Psychophysiological Touch Screen Stress Analyzer.

Figure 1:
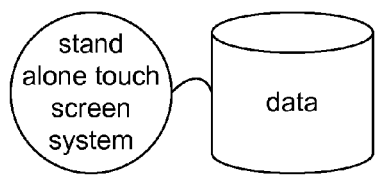
FIG. 1 is an example stand-alone system where the stimuli (questions, statements, pictures) are displayed on a touch screen computer through a series of computer generated screens.
Figure 2:
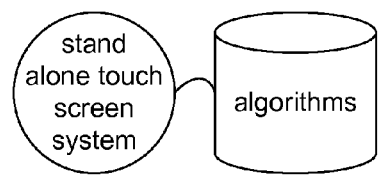
FIG. 2 is an example system where the computer within the touch screen also contains additional algorithms that perform an analysis on the touch screen data that will determine the person's emotional reactions patterns.

The first configuration is a stand-alone system where the stimuli (questions, statements, pictures) are displayed on a touch screen computer through a series of computer generated screens (FIG. 1). The person is to respond to each stimulus by touching their correct answer ("Yes" or "No") on the touch screen. The computer within the touch screen, through special computer algorithms, captures data generated when the person touches their answer to the stimulus on the touch screen. The computer within the touch screen also contains additional algorithms that perform an analysis on the touch screen data that will determine the person's emotional reactions patterns (FIG. 2). The analysis of the person's emotional reaction patterns is then displayed on the touch screen ranging from a low to severe reactions.

Figure 3:
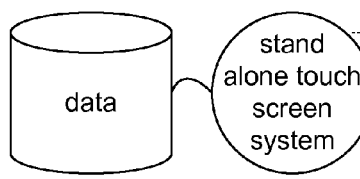
FIG. 3 is an example system where the stimuli (questions, statements, pictures) are displayed on a touch screen computer through a series of computer generated screens.
Figure 4:
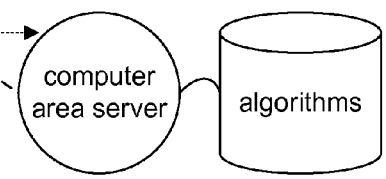
FIG. 4 is an example computer area server that is connected to the touch screen computer system through a private network.

The second configuration is a system where the stimuli (questions, statements, pictures) are displayed on a touch screen computer (FIG. 3) through a series of computer generated screens. The person is to respond to each stimulus by touching their correct answer ("Yes" or "No") on the touch screen. The computer within the touch screen, through special computer algorithms, captures data generated when the person touches their answer to the stimulus on the touch screen. The touch screen computer sends the touch data to a computer area server (FIG. 4) that is connected to the touch screen through a private network. The computer area server contains additional algorithms that will perform an analysis on the touch screen data. The analysis of this touch screen data will determine the person's emotional reactions patterns. The analysis of the person's emotional reaction patterns is then displayed on the area computer server screen ranging from a low to severe reactions.

Figure 5:
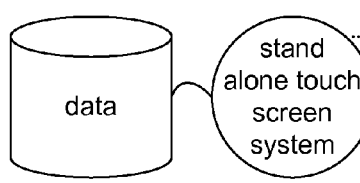
FIG. 5 is an example system where the stimuli (questions, statements, pictures) are displayed on a touch screen computer through a series of computer generated screens.
Figure 6:
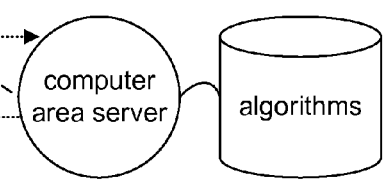
FIG. 6 is an example computer area server that is connected to the touch screen through a private network.
Figure 7:
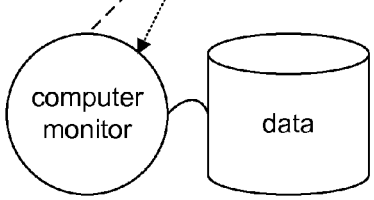
FIG. 7 is an example computer monitor to display the person's emotional reaction patterns on the computer screen ranging from a low to severe reactions.

The third configuration is a system where the stimuli (questions, statements, pictures) are displayed on a touch screen computer (FIG. 5) through a series of computer generated screens. The person is to respond to each stimulus by touching their correct answer ("Yes" or "No") on the touch screen. The computer within the touch screen, through special computer algorithms, captures data generated when the person touches their answer to the stimulus on the touch screen. The touch screen computer sends the touch data to a computer area server (FIG. 6) that is connected to the touch screen through a private network. The computer server contains additional algorithms that will perform an analysis on the touch screen data. The analysis of this touch screen data will determine the person's emotional reactions patterns. The emotional reaction data is then sent from the area computer server, through a private network, to a computer monitor (FIG. 7). The computer monitor will display the person's emotional reaction patterns on the computer screen ranging from a low to severe reactions.

The fourth configuration is a system where the stimuli (questions, statements, pictures) are displayed on a touch screen computer (FIG. 8) through a series of computer generated screens. The person is to respond to each stimulus by touching their correct answer ("Yes" or "No") on the touch screen. The computer within the touch screen, through special computer algorithms, captures data generated when the person touches their answer to the stimulus on the touch screen. The touch screen computer sends the touch data to a computer area server (FIG. 9) that is connected to the touch screen through a private network. The computer area server forwards the data to a computer master server (FIG. 10) through a secure network. The computer master server contains additional algorithms that will perform an analysis on the touch screen data. The analysis of this touch screen data will determine the person's emotional reactions patterns. The emotional reaction data is then sent from the area computer master server, through a private network, to a computer monitor (FIG. 11). The computer monitor will display the person's emotional reaction patterns on the computer screen ranging from a low to severe reactions.

The fifth configuration is a system where the stimuli (questions, statements, pictures) are displayed on a touch screen computer (FIG. 12) through a series of computer generated screens. The person is to respond to each stimulus by touching their correct answer ("Yes" or "No") on the touch screen. The computer within the touch screen, through special computer algorithms, captures data generated when the person touches their answer to the stimulus on the touch screen. The touch screen computer sends the touch data to a computer area server (FIG. 13) that is connected to the touch screen through a private network. The computer area server forwards the data to the computer master server (FIG. 14) through a secure network. The computer master server contains additional algorithms that will perform an analysis on the touch screen data. The analysis of this touch screen data will determine the person's emotional reactions patterns. The emotional reaction data is then sent from the computer master server back to the computer area server (FIG. 13) through a secure network. The emotional reaction data is then sent from the computer area server, through a private network, to a computer monitor (FIG. 15). The computer monitor will display the person's emotional reaction patterns on the computer screen ranging from a low to severe reactions.

Psychophysiological Touch Screen Stress Analyzer Study

A study was conducted to determine whether or not the Psychophysiological Touch Screen Stress Analyzer was capable of capturing a psychophysiological response to a stimulus.

In this study, a truth verification survey was administered by the Psychophysiological Touch Screen Stress Analyzer to a number of different subjects. This survey was adapted for the Psychophysiological Touch Screen Stress Analyzer from a psychological preconditioning questionnaire that had been developed for voice stress analysts and polygraph examiners.

The subject read the adapted questionnaire on the computer touch screen of the Psychophysiological Touch Screen Stress Analyzer. The subject answered each of the questions by touching the touch screen "yes" or "no" button at the bottom of the touch screen (the 'yes' button was green and 'no' button blue). After each touch screen answer button was touched by the subject, the next question was automatically displayed. Only the last 26 questions of the touch screen survey were analyzed to determine emotional reaction patterns (the same procedure followed in voice stress analysis and polygraph).

The following text was used on the computer touch screen of the Psychophysiological Touch Screen Stress Analyzer:

Introduction Screen:

This preliminary survey is to be completed prior to a formalized investigative interview. This process has been scientifically designed in such a manner as to identify those involved in committing acts of smuggling and/or terrorism. If the computer detects that you answers are false this will result in a more in-depth and extensive investigative interview.

TOUCH the green YES button to continue

Screen 1:

In this standardized computer generated survey, it is very important for you to read over each issue so that you will understand the meaning of each question pertaining to that issue.

There are approximately 69 survey questions.

If 'YES' is the right answer for you, PRESS the green 'YES' button.

If 'NO' is the right answer for you, PRESS the blue 'NO' button.

Use your same finger to answer every question.

Answer every question truthfully.

PRESS the green YES button to continue.

Screen 2:

SMUGGLING is the illegal transport across state or national boundaries of merchandise or persons liable to customs or to prohibition. Smuggling is to import or export or convey something secretly, in violation of the law, especially without payment of legal duty. This includes but is not necessary limited to: Luxury articles, monies and money laundering, counterfeiting, stolen art, electronic devices and software, illegal drugs and narcotics, weapons of destruction and any other specifically prohibited items.

This first issue concerns if you have a suspicion as to who could be involved in acts of SMUGGLING. What is meant by suspicion is that you have an idea in your mind, but do not know for sure, who could be involved in acts of SMUGGLING.

Do you suspect anyone, you personally know, of being involved in committing acts of SMUGGLING?

Screen 3:

This issue concerns if you actually know for sure who is involved in committing acts of SMUGGLING.

Do you know for sure, someone that you personally know, who is involved in committing acts of SMUGGLING?

Screen 4:

These next issues are directed only to you and concern if you are personally involved, in any manner, in committing acts SMUGGLING.

Are you personally involved in any manner in committing acts of SMUGGLING?

Screen 5:

Are you holding back any information about committing acts of SMUGGLING?

Screen 6:

Are you intentionally omitting or falsifying any information, or intentionally lying to any question about committing acts of SMUGGLING?

Screen 7:

Did you answer every question about SMUGGLING truthfully?

Screen 8:

TERRORISM is a deliberate attack by an individual or a group against a country, its institutions or its people—with the aim of intimidating them and damaging or destroying their political, economic or social structures.

TERRORISM includes but is not necessary limited to: Serious violence against people or danger to life, a serious risk to public health or safety, or serious damage to property. The list includes murder, kidnapping, seizing public transport, exploding bombs, releasing contaminating substances and interfering with computer networks.

This first issue concerns if you have a suspicion as to who could be involved in acts of TERRORISM. What is meant by suspicion is that you have an idea in your mind, but do not know for sure, who could be involved in acts of TERRORISM.

Do you suspect anyone, you personally know, of being involved in committing acts of TERRORISM?

Screen 9:

This issue concerns if you actually know for sure who is involved in committing acts of TERRORISM.

Do you know for sure, someone that you personally know, who is involved in committing acts of TERRORISM?

Screen 10:

These next issues are directed only to you and concern if you are personally involved, in any manner, in committing acts TERRORISM.

Are you personally involved in any manner in committing acts of TERRORISM?

Screen 11:

Are you holding back any information about committing acts of TERRORISM?

Screen 12:

Are you intentionally omitting or falsifying any information, or intentionally lying to any question about committing acts of TERRORISM?

Screen 13:

Did you answer every question about TERRORISM truthfully?

Screen 14:

Nearly everyone will have done or committed some act that could be considered illegal. This could be something very minor or something not so minor.

This interview process is only concerned with acts of SMUGGLING and TERRORISM. However, if you have been involved in past acts of SMUGGLING or TERRORISM, and you are very concerned about the possibility of it being discovered during this interview process, then this concern should be further discussed to prevent any significant emotional reaction patterns when answering any question pertaining to acts of SMUGGLING and TERRORISM under investigation. Therefore, it is very important that you truthfully answer the following question:

Is there some past act of SMUGGLING or TERRORISM in which you were involved that you are very concerned about being discovered during this interview process?

Screen 15:

In order to establish your present behavioral patterns (good to bad) we must attempt to establish your prior history of behavior. The purpose of the following questions is to establish this pattern; truthfulness is very important:

Before the age of 14, did you destroy something?

Screen 16:

Before the age of 14, did you intentionally destroy something?

Screen 17:

Before the age of 14, did you intentionally destroy something of great value that did not belong to you?

Screen 18:

Are you INTENTIONALLY lying to any question about destroying things before you were 14?

Screen 19:

Did you answer every question about destroying things before you were 14 truthfully?

Screen 20:

Before the age of 14, did you intentionally hurt someone?

Screen 21:

Before the age of 14, did you seriously hurt someone?

Screen 22:

Before the age of 14, did you seriously hurt someone who loved and trusted you?

Screen 23:

Are you INTENTIONALLY lying to any question about hurting someone before you were 14?

Screen 24:

Did you answer every question about hurting someone before you were 14 truthfully?

Screen 25:

Before the age of 17, did you destroy something?

Screen 26:

Before the age of 17, did you intentionally destroy something?

Screen 27:

Before the age of 17, did you intentionally destroy something of great value that did not belong to you?

Screen 28:

Are you INTENTIONALLY lying to any question about destroying things before you were 17?

Screen 29:

Did you answer every question about destroying things before you were 17 truthfully?

Screen 30:

Before the age of 17, did you intentionally hurt someone?

Screen 31:

Before the age of 17, did you seriously hurt someone?

Screen 32:

Before the age of 17, did you seriously hurt someone who loved and trusted you?

Screen 33:

Are you INTENTIONALLY lying to any question about hurting someone before you were 17?

Screen 34:

Did you answer every question about hurting someone before you were 17 truthfully?

Screen 35:

Are you INTENTIONALLY lying to any question about your behavior before you were 14?

Screen 36:

Did you answer every question about your behavior before you were 14 truthfully?

Screen 37:

Are you INTENTIONALLY lying to any question about your behavior before you were 17?

Screen 38:

Did you answer every question about your behavior before you were 17 truthfully?

Screen 39:

You will be asked the following questions in the examination to determine your present level of general nervous tension.

Are you a resident of this country?

Screen 40:

Do you live in this country?

Screen 41:

Regarding the day of the week, is today Sunday?

Screen 42:

After this next question you will be asked 26 questions that are scientifically designed through computer analysis to verify your answers on the survey you have just completed. There are no surprise or trick questions. You will only be asked questions referring to this survey.

Do you believe you will be asked a question in the following 26 questions about committing acts of SMUGGLING or TERRORISM, that has not been discussed with you?

Screen 43:

The following questions refer to survey questions you have just answered. It is important that you answer every question truthfully and not lie to any question from this point forward. After you read the question you have only 5 seconds to answer each question.

1 a. Are you a resident of this country?

Screen 44:

1 b. Do you live in this country?

Screen 45:

2a. Were you born in this country?

Screen 46:

2b. Are you a citizen of this country?

Screen 47:

3a. Regarding the day of the week, is it Sunday?

Screen 48:

3b. Is today Sunday?

Screen 49:

4a. Do you believe you will be asked a question about acts of SMUGGLING or TERRORISM that has not been discussed with you?

Screen 50:

4b. Are you concerned you will be asked a question about acts of TERRORISM and SMUGGLING that has not been discussed with you?

Screen 51:

5a. Regarding acts of SMUGGLING and TERRORISM, do you intend to lie to any question in this examination about SMUGGLING or TERRORISM activities?

Screen 52:

5b. Are you intending to lie about committing acts of SMUGGLING or TERRORISM?

Screen 53:

6a. Regarding your destroying something before the age of 17, are you intentionally omitting or falsifying information about destroying something before you were 17?

Screen 54:

6b. Are you lying to any question about destroying things before you were 17?

Screen 55:

7a. Regarding acts of SMUGGLING, are you personally involved, in any manner, in committing acts of SMUGGLING?

Screen 56:

7b. Are you lying about committing acts of SMUGGLING?

Screen 57:

8a. Regarding your hurting someone before the age of 17, are you intentionally omitting or falsifying information about hurting someone before you were 17?

Screen 58:

8b. Are you lying to any question about hurting someone before you were 17?

Screen 59:

9a. Regarding TERRORISM, are you personally involved, in an any manner, in committing acts of TERRORISM?

Screen 60:

9b. Are you lying about committing acts of TERRORISM?

Screen 61:

10a. Did you intentionally lie to any question in this examination about hurting someone or destroying things before you were 17?

Screen 62:

10b. Are you lie to any question about hurting someone or destroying things before you were 17?

Screen 63:

11a. Regarding acts of SMUGGLING and TERRORISM, did you intentionally lie to any question in this examination about SMUGGLING or TERRORISM activities?

Screen 64:

11b. Are you lying to any question about SMUGGLING or TERRORISM activities?

Screen 65:

12a. Is there something about SMUGGLING or TERRORISM activities that has not been discussed with you that you are very concerned about being discovered?

Screen 66:

12b. Are you concerned something else about acts of SMUGGLING or TERRORISM will be discovered?

Screen 67:

13a. Regarding the day of the week, is it Sunday?

Screen 68:

13b. Is today Sunday?

Screen 69:

Have you ever taken this survey before?

Screen 70:

That concludes this survey. Thank you.

Immediately after the Psychophysiological Touch Screen Stress Analyzer survey was completed and analyzed to determine emotional reaction patterns (Table 1), a Psychophysiological Voice Stress Analyzer examination was administered to each subject. The 26 questions asked were the same as questions on screens 43 to 68 administered by the Psychophysiological Touch Screen Stress Analyzer. The Psychophysiological Voice Stress Analyzer examination was prerecorded and played back through headphones place over the subject's ears. The subject's "yes" and "no" responses to each question were digitally recorded by means of boom microphone attached to the headphones. The microphone was place in a position just to right of the subject's mouth, approximately 1 inch. After the Psychophysiological Voice Stress Analyzer examination was administered, each "yes" and "no" response was analyzed to determine emotional reaction patterns (Table 2).

If the person's reaction patterns to the control questions average (Table 1 and 2, 16D) is greater than the reaction patterns to the relevant questions average (Table 1 and 2, 17D), then it can be assumed that the person made full disclosure concerning the relevant issue. However, if the person's reaction patterns to the relevant questions (Table 1 and 2, 17D) average is greater than the reaction patterns to the control questions average (Table 1 and 2, 16D), then it can be assumed that the person made did not full disclosure concerning the relevant issue.

TABLE 1

| PTSSA | A | B | C | D |
|---|---|---|---|---|
| 1 | Issue | Response A | Response B | Final Analysis |
| 2 | 1. US | 16.0 | 16.0 | 8.0 |
| 3 | 2. CA | 15.0 | 15.0 | 7.5 |
| 4 | 3. Sun | 15.0 | 16.0 | 10.8 |
| 5 | 4. O/I | 13.0 | 20.0 | 29.3 |
| 6 | 5. S/R | 21.0 | 13.0 | 8.5 |
| 7 | 6. Control | 12.0 | 29.0 | 61.3 |
| 8 | 7. Relevant | 28.0 | 12.0 | 10.0 |
| 9 | 8. Control | 14.0 | 34.0 | 72.1 |
| 10 | 9. Relevant | 32.0 | 18.0 | 12.5 |
| 11 | 10. Control | 20.0 | 34.0 | 55.6 |
| 12 | 11. Relevant | 33.0 | 15.0 | 12.0 |
| 13 | 12. O/I | 11.0 | 11.0 | 5.5 |
| 14 | 13. Sun | 14.0 | 11.0 | 6.3 |
| 15 | Test Avg | 19.4 | 19.4 | 25.8 |
| 16 | Control Avg | 15.4 | 32.4 | 63.0 |
| 17 | Relevant Avg | 31.0 | 15.0 | 11.5 |

TABLE 2

| PVSA | A | B | C | D |
|---|---|---|---|---|
| 1 | Issue | Response A | Response B | Final Analysis |
| 2 | 1. US | 61 | 46 | 70 |
| 3 | 2. CA | 43 | 33 | 49 |
| 4 | 3. Sun | 41 | 39 | 47 |
| 5 | 4. O/I | 52 | 61 | 80 |
| 6 | 5. S/R | 50 | 51 | 59 |
| 7 | 6. Control | 48 | 37 | 55 |
| 8 | 7. Relevant | 45 | 44 | 51 |
| 9 | 8. Control | 53 | 47 | 61 |
| 10 | 9. Relevant | 40 | 40 | 46 |
| 11 | 10. Control | 36 | 27 | 41 |
| 12 | 11. Relevant | 27 | 24 | 31 |
| 13 | 12. O/I | 25 | 24 | 29 |
| 14 | 13. Sun | 24 | 31 | 43 |
| 15 | Test Avg | 42 | 39 | 50 |
| 16 | Control Avg | 46 | 37 | 52 |
| 17 | Relevant Avg | 37 | 36 | 43 |

CONCLUSION

There was 100% correlation between the Psychophysiological Voice Stress Analyzer (Table 2) and the Psychophysiological Touch Screen Stress Analyzer (Table 1) concerning the Final Analysis Control Avg and the Final Analysis Relevant Avg in all test subjects. This data proves, beyond a reasonable doubt, that when the subject touches the specialized computer touch screen, in response to the stimulus displayed on the touch screen, the subject's psychophysiological response was captured.

The invention claimed is:

1. A system for analyzing emotional stress of a subject, the system comprising:
   a non-transitory computer readable medium configured to store executable programmed modules and information;
   a processor communicatively coupled with the non-transitory computer readable medium and configured to execute programmed modules stored therein;
   a computer monitor communicatively coupled with the processor and configured to display information to a subject;
   a touch input device communicatively coupled with the processor and configured to receive an input from the subject;
   a survey module stored in the non-transitory computer readable medium and executable by the processor, the survey module configured to provide a series of questions on the computer monitor and store in the non-transitory computer readable medium responses to said series of questions received from the subject via said touch input device; and
   an analysis module configured to analyze each response to said series of questions and determine a muscle tremor reaction pattern calculated by a pressure value and a time duration value of the responses received from the subject, the analysis module further configured to calculate an emotional reaction of the subject to each question based on said muscle tremor reaction pattern, and compare the calculated emotional reaction of a first portion of questions in said series of questions to the calculated emotional reaction of a second portion of questions in said series of questions.

2. A system for analyzing emotional stress of a subject, the system comprising:
   at least one subject interface station including a computer monitor configured to display a series of questions to a subject and a touch input device configured to receive corresponding responses to said series of questions received from the subject; and
   an analysis server configured to receive and store information from said at least one subject interface station related to one or more series of questions and said corresponding responses in a non-transitory computer readable medium,
   wherein the analysis server is configured to analyze responses corresponding to the one or more series of questions and store in said non-transitory computer readable medium muscle tremor reaction patterns calculated by a pressure value and a time duration value of said responses,
   wherein the analysis server is further configured to calculate and store in said non-transitory computer readable medium emotional reaction data based on said muscle tremor reaction patterns,
   wherein the analysis server is further configured to compare a first portion of the calculated emotional reaction data to a second portion of the calculated emotional reaction data.

3. A method for analyzing emotional stress of a subject, comprising:
   presenting information on a monitor device;
   sensing a touch of the subject on a touch input device in response to presenting said information on the monitor device;
   determining, for each responsive touch on the touch input device:
      a pressure value of the responsive touch;
      a time duration value of the responsive touch; and
      a muscle tremor reaction pattern based on the pressure value of the responsive touch and the time duration value of the responsive touch;

providing at least the pressure value and the time duration value to an analysis server via a network; and storing the pressure value, time duration value and muscle tremor reaction pattern in a non-transitory computer readable medium by said analysis server.

4. The method of claim 3, wherein the muscle tremor reaction pattern based on the pressure value of the responsive touch and the time duration value of the responsive touch is determined by said analysis server.

5. The method of claim 3, further comprising calculating an emotional reaction of the subject based on said muscle tremor reaction and time duration values.

6. The method of claim 3, further comprising determining, for each responsive touch on the touch input device, a location value of the responsive touch, wherein the location value represents a location on the touch input device.

7. The method of claim 6, further comprising providing the location value to the analysis server via the network.

8. The method of claim 6, further comprising calculating an emotional reaction to said question based on said location, muscle tremor reaction and time duration values.

9. The method of claim 3, further comprising providing the muscle tremor reaction pattern to the analysis server via the network.

10. The method of claim 3, wherein said information presented on the monitor device comprises a first series of questions, further comprising calculating, by the analysis server, an emotional reaction baseline from plural responsive touches to said first series of questions.

11. The method of claim 10, wherein said information presented on the monitor device comprises a second series of questions that is different from said first series of questions, further comprising comparing, by the analysis server, plural responses to said second series of questions to said emotional reaction baseline.

* * * * *